United States Patent [19]

Ennis et al.

[11] Patent Number: 5,059,443
[45] Date of Patent: Oct. 22, 1991

[54] ESTERIFIED ETHOXYLATED ALKYL GLYCOSIDES USEFUL IN LOW CALORIE FAT-CONTAINING FOOD COMPOSITIONS

[75] Inventors: John L. Ennis, Arlington; Peter W. Kopf, Sudbury; Stephen E. Rudolph, Carlisle; Martin F. van Buren, Chelmsford, all of Mass.

[73] Assignee: The Procter & Gamble Co., Cincinnati, Ohio

[21] Appl. No.: 400,428

[22] Filed: Aug. 30, 1989

[51] Int. Cl.$^5$ .............................................. C07H 15/00
[52] U.S. Cl. .................................... 426/531; 426/601; 426/611; 426/804; 536/18.3
[58] Field of Search ............... 426/531, 601, 611, 804; 536/18.3

[56] References Cited

U.S. PATENT DOCUMENTS

| | | | |
|---|---|---|---|
| 4,137,401 | 1/1979 | Lemieuex et al. | 536/116 |
| 4,264,478 | 4/1981 | Seldner | 252/522 R |
| 4,324,703 | 4/1982 | Seldner | 252/522 R |
| 4,364,930 | 12/1982 | Griat et al. | 424/81 |
| 4,687,843 | 8/1987 | Smolin et al. | 536/18.3 |
| 4,840,815 | 6/1989 | Meyer et al. | 426/611 |
| 4,849,242 | 7/1989 | Kershner | 426/601 |
| 4,861,613 | 8/1989 | White et al. | 426/611 |

FOREIGN PATENT DOCUMENTS

| | | | |
|---|---|---|---|
| 254547 | of 1988 | European Pat. Off. | |
| 325010 | 7/1989 | European Pat. Off. | 426/804 |

OTHER PUBLICATIONS

Akoh et al., "Synthesis and Properties of Alkyl Glycoside and Stachyose Fatty Acid Polyesters", *JAOCS*, vol. 66, No. 9, pp. 1295–1301 (Sep. 1989).

Akoh et al., "Preliminary Raffinose Polyester and Methyl Glucoside Polyester Feeding Trials with Mice", *Nutrition Reports International*, vol. 39, No. 4, pp. 659–666 (Apr. 1989).

The National Institutes of Health Consensus Development Conference, "Lowering Blood Cholesterol to Prevent Heart Disease", *JAMA*, vol. 253, No. 14, pp. 2080–2086 (1985).

Specifications for Glucam E-20, Amerchol, 136 Talmadge Rd., P.O. Box 4051, Edison, N.J. 08818-4051.

Haumann, "Getting the Fat Out", *JAOCS*, vol. 63, No. 3, pp. 278–288 (Mar. 1986).

LaBarge, "The Search for a Low-Caloric Oil", *Food Technology*, pp. 84–90 (Jan. 1988).

*Primary Examiner*—Donald E. Czaja
*Assistant Examiner*—Evan Federman
*Attorney, Agent, or Firm*—Gary M. Sutter; John M. Howell; Richard C. Witte

[57] ABSTRACT

The invention is a low calorie fat-containing food composition. From 10% to 100% of the fat ingredients consist of alkoxylated alkyl glycosides esterified with fatty acids. Between 1 and about 50 alkoxyl groups are attached by ether linkages to each alkyl glycoside molecule, and not more than about 12 alkoxyl groups are attached to each attachment site of an alkyl glycoside molecule. Each alkoxylated alkyl glycoside molecule is esterified with between 4 and 7 fatty acid groups, the fatty acids containing between about 2 and about 24 carbon atoms. Preferred alkoxylated alkyl glycosides are ethoxylated methyl glucosides.

12 Claims, No Drawings

ESTERIFIED ETHOXYLATED ALKYL GLYCOSIDES USEFUL IN LOW CALORIE FAT-CONTAINING FOOD COMPOSITIONS

TECHNICAL FIELD

The present invention relates to the field of low calorie fat and oil substitutes. Specifically, the invention relates to alkoxylated alkyl glycosides that are esterified with fatty acids. These compounds have been found to be useful for replacing triglyceride fats in low calorie fat-containing food compositions.

BACKGROUND OF THE INVENTION

The consumption of large amounts of triglyceride fats has been linked to various health problems. For example, one of the most common metabolic problems among people today is obesity. This condition is primarily due to ingestion of a greater number of calories than are expended. Fat is the most concentrated form of energy in the diet, with each gram of fat supplying approximately nine calories, and triglyceride fats constitute about 90% of the total fat consumed in the average diet.

The National Institutes of Health Consensus Development Conference, "Lowering Blood Cholesterol to Prevent Heart Disease," JAMA, Vol. 253, No. 14, pp. 2080-2086 (1985), concluded that elevation of blood cholesterol levels is a major cause of coronary artery disease, and recommended a reduction in the amount of fat eaten to reduce blood serum cholesterol levels.

Hence, there is a need for ways t reduce the amount of triglyceride fats in the diet, in order to reduce the health risks associated with these fats.

Numerous fat substitutes are known to the art. A review of some of the approaches tried for replacing fats and oils is given in an article by Haumann, "Getting the Fat Out," *JAOCS*, Vol. 63, No. 3, pp. 278-288 (March 1986). Various approaches and products that have been suggested for replacement of the fat content of foods are examined by LaBarge in "The Search for a Low-Caloric Oil," *Food Technology*, pp. 84-90 (January 1988).

A partial list of some of the reduced calorie fat substitutes known to the art includes the following: sugar and sugar alcohol fatty acid polyesters (U.S. Pat. No. 3,600,186 to Mattson et al., issued Aug. 17, 1971); fatty alcohol esters of polycarboxylic acids (U.S. Pat. No. 4,508,746 to Hamm, issued Apr. 2, 1985); fatty polyethers of polyglycerol (U.S. Pat. No. 3,932,532 to Hunter et al., issued Jan. 13, 1976) (food use disclosed in German Patent 207,070, issued Feb. 15, 1984); ethers and ether-esters of polyols containing the neopentyl moiety (U.S. Pat. No. 2,962,419 to Minich, issued Nov. 29, 1960); fatty alcohol diesters of dicarboxylic acids such as malonic and succinic acid (U.S. Pat. No. 4,582,927 of Fulcher, issued Apr. 15, 1986); triglyceride esters of alpha branched chain-alkyl carboxylic acids (U.S. Pat. No. 3,579,548 to Whyte, issued May 18, 1971); fatty acid diglyceride, diesters of dibasic acids (U.S. Pat. No. 2,874,175 to Feuge et al.); polyorganosiloxanes (European Patent Application 205,273 to Frye); alpha-acylated glycerides (U.S. Pat. No. 4,582,715 to Volpenhein); medium chain triglycerides; highly esterified polyglycerol esters; acetin fats; plant sterol esters; N-Oil; polyoxyethylene esters; jojoba esters; mono/diglycerides of fatty acids; and mono/diglycerides of short-chain dibasic acids.

Esterified propoxylated methyl glycosides are also known to the art. U.S. Pat. No. 4,687,843 to Smolin et al., issued Aug. 18, 1987, discloses esterified propoxylated methyl glucoside compositions used as skin moisturizers and emollients in skin care formulations. It is not suggested that the glucosides can be used as a fat substitute in low calorie food compositions.

U.S. Pat. Nos. 4,264,478 and 4,324,703 to Seldner, issued Apr. 28, 1981 and Apr. 13, 1982, disclose the use of alkoxylated (particularly ethoxylated and propoxylated) methyl glycosides as fragrance fixatives. The esters are not disclosed. Again, there is no mention of using the glucosides as low calorie fat substitutes.

Other related art includes European Patent Application 254,547 to White et al., published Jan. 27, 1988, which discloses esterified derivatives of epoxylated polyols for use as fat substitutes. The polyols have from 1 to 8 primary hydroxyls and from 0 to 8 secondary and tertiary hydroxyls, the sum of the hydroxyls being from 3 to 8. Examples of disclosed polyols are sugars, glycerides and saccharides. Glucose and other sugars are disclosed but not alkyl glycosides.

U.S. Pat. No. 4,364,930 to Griat et al., issued Dec. 21, 1982 discloses, as emulsifiers, mono- or di-alkyl carboxylic acid esters of polyethoxylenated α-methyl glucosides. The ethoxylation is with 10-30 moles of ethylene oxide and the alkyl moieties contain 11-21 carbon atoms. The disclosed use for the emulsifiers is in cosmetic and topical pharmaceutical compositions. Food use is not disclosed.

One of the main problems in attempting to formulate fat substitute compounds that have decreased absorbability and thus low calorie properties is to maintain the desirable and conventional physical properties of edible fat. Thus, to be a practical low calorie fat substitute, a compound must resemble conventional triglyceride fat, and have the same utility in various fat-containing food compositions such as shortening, margarine, cake mixes, and the like, and be useful in frying or baking.

None of the above-mentioned references suggests that alkoxylated alkyl glycosides esterified with fatty acids are particularly suitable for use as low calorie fat substitutes in fat-containing food compositions. It is known in the art that esterified propoxylated methyl glucosides can be used in skin care formulations. However, the compounds of the present invention have now surprisingly been found to have desirable organoleptic and other physical properties that make them well-suited as fat substitutes. This is so even though the structures of the compounds are significantly different from those of triglyceride fats.

Moreover, the compounds of the invention have now been found to be resistant to hydrolysis and therefore nondigestible. Accordingly, the compounds contain zero calories, in contrast to the nine calories per gram in triglyceride fats.

It is, therefore, an object of the present invention to provide esterified alkoxylated alkyl glycosides that have organoleptic properties making them suitable for use as fat substitutes.

It is another object of the present invention to provide fat substitutes that are resistant to hydrolysis and therefore nondigestible and noncaloric.

It is a further object of the present invention to provide food compositions containing these nondigestible fat substitutes.

These and other objects of the present invention will become evident from the disclosure herein.

All parts, percentages and ratios used herein are by weight unless otherwise indicated.

SUMMARY OF THE INVENTION

The present invention relates to a low calorie food composition comprising fat and non-fat ingredients wherein from 10% to 100% of the fat ingredients consist essentially of alkoxylated alkyl glycosides esterified with fatty acids. Between 1 and about 50 alkoxyl groups are attached by ether linkages to each alkyl glycoside molecule, and not more than about 12 alkoxyl groups are attached to each attachment site of an alkyl glycoside molecule. Each alkoxylated alkyl glycoside molecule is esterified with between 4 and 7 fatty acid groups, the fatty acids containing between about 2 and about 24 carbon atoms. Preferred alkoxylated alkyl glycosides are propoxylated and ethoxylated methyl glucosides.

DETAILED DESCRIPTION OF THE INVENTION

The present invention relates to certain esterified alkoxylated alkyl glycosides which have now been surprisingly discovered to be useful as fat substitutes in low calorie fat-containing food compositions. The food compositions comprise: (a) non-fat ingredients; and (b) fat ingredients, from about 10% to 100% by weight of the fat ingredients consisting essentially of the esterified alkoxylated alkyl glycosides of the present invention.

The compounds of the present invention (and fat-containing food compositions containing these compounds) have desirable physical properties and palatability compared to ordinary triglyceride fats and compositions containing same. However, these compounds have a substantially lower effective caloric value than triglyceride fats (zero calories/gram versus nine calories/gram) because they are not digested or absorbed in the intestinal tract.

A. Definitions

By "alkoxylated" alkyl glycosides, as used herein, is meant that the alkyl glycosides are reacted with cyclic ether compounds selected from the group consisting of propylene oxide, ethylene oxide, 1-butene oxide, cis-2-butene oxide, trans-2-butene oxide, 1-hexene oxide, tert-butylethylene oxide, cyclohexene oxide, 1-octene oxide, cyclohexylethylene oxide, styrene oxide, 1-decene oxide, 1-octadecene oxide, isobutylene oxide, epichlorohydrin, epibromohydrin, epiiodohydrin, perfluoropropylene oxide, cyclopentene oxide, 1-pentene oxide, oxetane, oxetane derivatives, and mixtures thereof, to form hydroxyl terminated ether compounds. With the exception of oxetane and oxetane derivatives, these compounds are all epoxides. The ring structures of the compounds contain 2 to 4 carbon atoms and an oxygen atom. Preferred compounds for use herein are propylene oxide, ethylene oxide, and mixtures thereof. These compounds and their chemistry are known to those skilled in the art. See, e.g., *Encyclopedia of Polymer Science and Technology*, 1st Ed., Vol 6, 1,2-Epoxide Polymers, pp. 108, 154, 186, 187 and 192, Interscience Publishers, New York (1967), and 2nd Ed., Vol. 6, pp. 276–277 (1985): and Frisch, *Cyclic Monomers*, Vol. XXVI of the High Polymers Series, pp. 8–9, 54–59 and 100–102, Wiley-Interscience, New York (1972).

By "alkoxyl groups", as used herein, is meant the cyclic ether compounds disclosed above after they have reacted with and become attached to an alkyl glycoside through ether linkages. For example, propylene oxide reacts with methyl glucoside to form propoxylated methyl glucoside; the propylene oxide changes into a "propoxyl" group during the reaction. Similarly, ethylene oxide becomes an "ethoxyl" group. Hence, the alkoxyl groups are "derived from" the above-mentioned cyclic ether compounds. This is well understood in the art; see, e.g., U.S. Pat. Nos. 4,624,478 and 4,324,703 to Seldner, issued Apr. 28, 1981 and Apr. 13, 1982 (incorporated by reference herein).

As discussed hereinbelow, between 1 and about 50 alkoxyl groups are attached to each alkyl glycoside molecule. When more than one alkoxyl group is attached to a single attachment site of the alkyl glycoside, the alkoxyl groups are polymerized in the form of a chain. This chemistry is known to those skilled in the art. See, e.g., Frisch, *Cyclic Monomers*, Vol. XXVI of High Polymers Series, Wiley-Interscience, New York, pp. 36–39 (1972); and Saunders and Frisch, *Polyurethanes: Chemistry and Technology*. Part I, Interscience Publishers, New York, pp. 32–43 (1962).

By "alkyl glycoside", as used herein, is meant a glycoside molecule that has one alkyl group attached through a hemiacetal bond, where the alkyl group contains between 1 and 22 carbon atoms. (The alkyl glycoside is prepared by reaction of a glycoside with an alcohol. For example, glucoside reacted with methanol yields methyl glucoside.) Preferred alkyl glycosides for use in the invention are methyl glucoside, ethyl glucoside, and propyl glucoside, and mixtures thereof. Most preferred is methyl glucoside.

By "glycoside", as used herein, is meant the acetal formed by interaction of an alcohol with a carbonyl group of a monosaccharide or disaccharide (excluding polysaccharides). The monosaccharides include, but are not limited to, glucose, fructose, mannose, arabinose, gulose, xylose, lyxose, erythrose, threose, galactose and sorbose. The disaccharides include, but are not limited to, maltose, lactose, cellobiose and sucrose. The glycoside derived from glucose is termed a "glucoside".

B. Esterified Alkoxylated Alkyl Glycosides

A fat substitute according to the present invention is a fatty acid ester of an alkoxylated alkyl glycoside, wherein:

(a) the glycoside molecule has one alkyl group attached to it, and wherein the alkyl group contains between 1 and 20 carbon atoms;

(b) between 1 and about 50 alkoxyl groups are attached by ether linkages to each alkyl glycoside molecule, and not more than about 12 alkoxyl groups are attached to each attachment site of an alkyl glycoside molecule;

(c) each alkoxylated alkyl glycoside molecule is esterified with between 4 and 7 fatty acid groups, and wherein the fatty acids contain between about 2 and about 24 carbon atoms; and (d) the alkoxyl groups are derived from cyclic ethers selected from the group consisting of propylene oxide, ethylene oxide, 1-butene oxide, cis-2-butene oxide, trans-2-butene oxide, 1-hexene oxide, tert-butylethylene oxide, cyclohexene oxide, 1-octene oxide, cyclohexylethylene oxide, styrene oxide, 1-decene oxide, 1-octadecene oxide, isobutylene oxide, epichlorohydrin, epibromohydrin, epiiodohydrin, perfluoropropylene oxide, cyclopentene oxide, 1-pentene oxide, oxetane, oxetane derivatives, and mixtures thereof.

An esterified propoxylated methyl glucoside according to the present invention has the following structural formula:

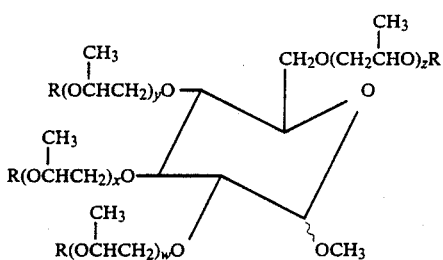

wherein:
w+x+y+z is from 1 to about 50; each w, x, y, and z has a numerical value of not more than about 12; and each R is a fatty acyl group having between about 2 and about 24 carbon atoms.

Similarly, an esterified ethoxylated methyl glucoside of the invention has the following structural formula:

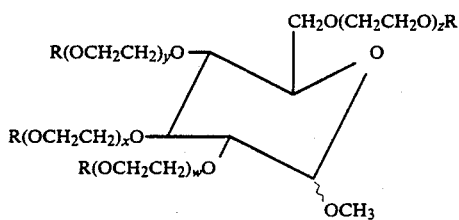

wherein
w+x+y+z is from 1 to about 50; each w, x, y, and z has a numerical value of not more than about 12; and each R is a fatty acid group having between about 2 and about 24 carbon atoms.

It has been discovered that the total number of alkoxyl groups attached to each alkyl glycoside molecule (w+x+y+z in the structural formulas above) must be between 1 and about 50. Compounds with more than 50 alkoxyl groups have more polyether character than is desirable in a fat substitute. The compounds contain at least one alkoxyl group; it is hypothesized that an alkoxylated structure is more suitable as a fat substitute than a structure with no alkoxyl groups because placing the ester linkage farther away from the glycoside causes a disruption of lipase mediated hydrolysis. It is more difficult for the lipase enzymes to handle these compounds and initiate digestion. Preferably, the total number of alkoxyl groups per molecule is between about 6 and about 30, more preferably between about 10 and about 24.

Moreover, attachment of fatty acid ester groups at the ends of the alkoxyl groups produces a large hydrophilic center in the compounds. As a result, it is believed that the compounds form better emulsions in the gut and thus are more compatible with the gastrointestinal tract so that fewer GI problems such as oil separation will occur.

Not more than about 12 alkoxyl groups are attached to each attachment site of an alkyl glycoside molecule. (With reference to the above structural formulas, each w, x, y and z has a numerical value of not more than about 12.) This range is important for producing compounds that are not digestible, and that have other properties similar or identical to those of triglyceride fats. Preferably between about 1 and about 8 alkoxyl groups are attached to each attachment site, more preferably between about 2 and about 6, and most preferably about 5.

As shown in the structural formulas above, the akloxylated alkyl glycoside molecules are esterified with fatty acid groups having between about 2 and about 24 carbon atoms. It has been discovered that the alkoxylated alkyl glycosides must be esterified with between 4 and 7 fatty acid groups to be effective noncaloric fat substitutes for use in the present invention. (The alkoxylated alkyl glycosides will have between 4 and 7 sites available for reaction with fatty acids depending on the type of glycoside, as is well understood in the art.)

The fatty acids are $C_2$ to $C_{24}$ in carbon chain length. $C_2$ to $C_{24}$ fatty acids will impart the desired organoleptic character to the polyester compounds. Preferred fatty acids are $C_8$ to $C_{22}$, more preferred are $C_{14}$ to $C_{18}$, and most preferred are $C_{18}$. Examples of such fatty acids include acetic, butyric, caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids, and can be saturated or unsaturated, including positional or geometrical isomers (e.g., cis and trans isomers). Oleic and stearic acids, and mixtures thereof, are especially preferred.

The glucosides used in the present invention are preferably α-alkyl glucosides in structure rather than β-alkyl glucosides. It is believed that the α-alkyl structure is somewhat more highly resistant to hydrolysis because of its stable acetal structure. Preferably at least about 70% α-alkyl glucosides are used in the present fat substitute, more preferably at least about 80%.

U.S. Pat. No. 4,687,843 to Smolin et al. (assigned to Amerchol Corporation), issued Aug. 18, 1987 (incorporated by reference herein), discloses fatty acid esters of propoxylated methyl glucosides. See particularly column 2, line 48 to column 3, line 33. Additionally, U.S. Pat. Nos. 4,264,478 and 4,324,703 to Seldner (assigned to Amerchol Corporation), issued Apr.28, 1981 and Apr. 13, 1982 (both incorporated by reference herein), disclose alkoxylated (particularly ethoxylated and propoxylated) methyl glucosides. As stated in the Seldner '478 patent at column 3, lines 44–59, these ethoxylated and propoxylated glucosides are commercially available from Amerchol Corporation, Talmadge Road, Edison, N.J. under the trademark GLUCAM ® methyl glucoside polyol. GLUCAM ® E-10 and GLUCAM ® E-20 are the 10 and 20 mole ethoxylates, respectively. GLUCAM ® P-10 and GLUCAM ® P-20 are the 10 and 20 mole propoxylates, respectively. GLUCAM ® P-20 is, for example, prepared by reacting 20 moles of propylene oxide with 1 mole of methyl glucoside.

C. Methods for Making the Esterified Alkoxylated Alkyl Glycosides

For making the fat substitutes of the present invention, the starting material is an alkoxylated alkyl glycoside, preferably a propoxylated methyl glucoside or an ethoxylated methyl glucoside. As discussed hereinabove, these latter compounds are commercially available from Amerchol Corporation, Talmadge Road, Edison, N.J. under the trademark GLUCAM ®, where GLUCAM ® E-10 and GLUCAM ® E-20 are the 10 and 20 mole ethoxylates, and GLUCAM ® P-10 and GLUCAM ® P-20 are the 10 and 20 mole propoxylates. GLUCAM® P-20 and GLUCAM® P-10 have been assigned the names PPG-20 Methyl Glucose Ether and PPG-10 Methyl Glucose Ether by the Cosmetic, Toiletry and Fragrance Association (CTFA), and GLUCAM® E-20 and E-10 have been assigned the names Methyl Gluceth-20 and -10. The propoxylates have been assigned a Chemical Abstracts Service (CAS) Registry No. 61849-72-7, and the ethoxylates No. 68239-42-9. GLUCAM® is believed to have a ratio of about 8:1 α-methyl to β-methyl structure. For further details, see U.S. Pat. Nos. 4,264,478, 4,324,703, and 4,687,843 assigned to Amerchol Corporation, issued Apr. 28, 1981, Apr. 13, 1982 and Aug. 18, 1987 (incorporated by reference.)

The alkoxylated alkyl glycoside is esterified with fatty acids by any of a variety of general esterification methods well known to those skilled in the art. These methods include: acylation with a fatty acid chloride, acylation with a fatty acid anhydride, acylation with a fatty acid per se, and transesterification with another ester such as methyl, ethyl or glycerol. The preferred method is acylation with a fatty acid chloride, as disclosed in Examples 1-3 hereinafter.

Example 1 shows the preparation of an ethoxylated methyl glucoside tetraoleate. GLUCAM® E-20 (49.85 grams) is first diluted in a solvent mixture of 50 ml DMF and 100 ml pyridine. While this DMF/pyridine mixture is the preferred solvent, it is anticipated that other organic solvents known to those skilled in the art could also be used. This solution is charged to a flask equipped with a reflux condenser, dry $N_2$ purge, and a magnetic stirrer.

The GLUCAM® E-20 solution is heated to a temperature between 40° C. (104° F.) and 45° C. (113° F.) while the flask is purged with nitrogen. While 40°-45° C. (104°-113° F.) is the preferred temperature range, the practical operating range can vary from 0° C. (32° F.) to the solvent reflux temperature; the upper limit will vary with the solvent composition (it is about 115° C. (239° F.) for the DMF/pyridine solvent). The reaction is preferably conducted under nitrogen. However, other inert gases can be used instead of nitrogen, such as helium or argon.

Separately, oleoyl chloride (66.2 grams) is diluted in 225 ml of methylene chloride. Chlorides of other fatty acids besides oleic acid are also suitable for use in the present invention, but oleic acid is the most preferred fatty acid while stearic acid is second most preferred. Other suitable $C_2$ to $C_{24}$ fatty acids are described hereinabove. The preferred solvent for the fatty acid chloride is methylene chloride, but other suitable solvents can be used that are known to those skilled in the art.

The mole ratio of oleoyl chloride to ethoxylated methyl glucoside can range between about 4.0 and about 4.4, preferably between about 4.1 and about 4.3.

The oleoyl chloride solution is added dropwise to the stirred, heated GLUCAM® solution under nitrogen, over a period of about 1.5 hours. The time for addition can vary between about 1 hour and about 3 hours.

After completion of the addition, the reactants are heated to 55° C. (131° F.) and reacted for 6 hours. The reaction temperature can vary between about 35° C. (95° F.) and the solvent reflux temperature (about 59° C. (138° F.) in this example). When ethoxylated glucosides are the starting material, the reaction time is between about 6 hours and about 8 hours, while a longer heated reaction time is needed for propoxylated glucosides, between about 8 hours and about 24 hours.

After the reaction is complete, the reactants are cooled to about room temperature and stirred under nitrogen for about 16 hours (this time typically varies between about 1 hour and about 60 hours, but the time of stirring under nitrogen is not critical to the process).

The product is isolated by any suitable method known to the art. Example 1 hereinbelow discloses details of the preferred method for isolating an ethoxylated methyl glucoside tetraoleate, while Example 3 discloses the preferred method for isolating the tetrastearate.

D. Resistance to Hydrolysis of the Present Esterified Alkoxylated Alkyl Glycosides The esterified alkoxylated methyl glucoside products of Examples 1 and 2 hereinbelow are measured for resistance to hydrolysis by two techniques: (1) a 30-minute digest with commercial porcine lipase, and (2) a pH stat hydrolysis rate measurement with rat pancreatic juice.

(1) Digest with Steapsin:

The initial screening of these products is performed with steapsin, a porcine pancreatic lipase, in a digest medium of Tris buffer, pH 8.0. The substrate (glucoside product), medium, and enzyme are emulsified by vigorous shaking on a wrist-action shaker for thirty minutes at room temperature. The measurement of hydrolysis is by titration with a standardized base solution using phenophthalein indicator. The free fatty acid released by enzyme is the equivalent of the base consumed in the titration and is expressed as a percent of the total fatty acid initially present in the product. The data presented in Table I are the result of initial stability testing with steapsin. The data suggest that little or no hydrolysis occurs in the presence of the porcine lipase. (There is no titration for the presence of free acid in the samples prior to digestion by lipase, and the apparent low percent hydrolysis could be even lower if this assessment is made.)

TABLE I

| Product | M. W. (g/mol) | Percent Hydrolysis with Commerical Lipase | | | | | | % Hydrolysis of Ester Bonds |
| --- | --- | --- | --- | --- | --- | --- | --- | --- |
| | | Fat (mg) | Fat (umol) | F. A. (umol) | KOH (ml) | KOH (umol) | F.F.A. (umol) | |
| Example 1 | 434 | 549 | 1266 | 5064 | 0.65 | 62 | 62 | 1.2 |
| Example 2 | — | 500 | — | — | 0.25 | 24 | 24 | 1.4 |
| Crisco Oil | 885 | 654 | 738 | 2216 | 14.20 | 1346 | 1346 | 60.7 |

(2) pH Stat Measurement with Pancreatic Juice:

The in vitro lipolysis of the esterified alkoxylated methyl glucoside products of Examples 1-3 is examined using a pH Stat recording titrator. A nominal 1 gram of glucoside product (substrate) is added to 70 ml of histidine buffer medium containing 1 ml of a 1% sodium taurocholate solution. The medium is emulsified in a 100 ml 4-neck roundbottom flask by vigorous shaking with a wrist-action shaker for 10 minutes. The flask is then fitted with pH electrode, titrant delivery tube, and propeller stirrer. The reaction is initiated by delivery of 1.0 ml of enzyme (bile-pancreatic combination fluid) into the stirred emulsion. The pH is maintained at 9.0 by the addition of 0.1 N KOH delivered from a Metrohm pH stat-titrator system. The linear portion of the plot resulting from added base versus time during the first 1-4 minutes of the reaction is used to determine the rate of fatty acid production for each product.

The digestibilities of the glucoside products are shown in Table II below. In contrast to the porcine lipase, the bile-pancreatic combination fluid contains nonspecific lipase which would hydrolyze both primary and secondary esters and, therefore, might potentially hydrolyze any ester bond in the test products. Evidence for the activity of nonspecific lipase in the combination fluid is seen in hydrolysis tracings of the substrates. The assessment of hydrolytic stability by pH-stat tracings essentially confirms the preliminary findings with porcine pancreatic lipase.

TABLE II

| Product | Sample Wt. (gm) | Rate of Hydrolysis (ueq KOH/min) |
| --- | --- | --- |
| Example 1 | 1.0657 | 0.0 |
| Example 2 | 1.0220 | 5.0 |
| Example 3 | 1.1970 | 0.0 |

E. Low Calorie Fat-Containing Food Compositions

The esterified alkoxylated alkyl glycosides of the present invention can be used as partial or total replacements for normal triglyceride fats in any fat-containing food composition to provide low calorie benefits. The amount of the present compounds included in the fat will depend upon the food composition and the low calorie effect desired. In order to obtain a significant low calorie effect, it is necessary that at least about 10% of the fat in the food composition comprise the present compounds. On the other hand, very low calorie and thus highly desirable food compositions of the present invention are obtained when the fat comprises up to 100% of the present compounds.

The compounds of the present invention are useful in a wide variety of food and beverage products. For example, the compounds can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods and other baked salted snacks.

In addition to their uses in baked goods, the present compounds can be used alone or in combination with other regular, reduced calorie or zero calorie fats to make shortening and oil products. The other fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oils. The present compounds can be used to make foods that are fried in oil (e.g., Pringle's potato chips, corn chips, tortilla chips, other fried farinaceous snack foods, French fries, doughnuts, and fried chicken).

Imitation dairy products can also be made (e.g., butter, ice cream and other fat-containing frozen desserts, yogurt, and cheeses, including natural cheeses, processed cheeses, cream cheese, cottage cheese, cheese foods and cheese spread, milk, cream, sour cream, butter milk, and coffee creamer).

The present compounds are also useful for making meat products (e.g, hamburgers, hot dogs, frankfurters, wieners, sausages, bologna and other luncheon meats, canned meats, including pasta/meat products, stews, sandwich spreads, and canned fish), meat analogs, tofu, and various kinds of protein spreads.

Sweet goods and confections can also be made (e.g., candies, chocolates, chocolate confections, frostings and icings, syrups, cream fillings, and fruit fillings), as well as nut butters and various kinds of soups, dips, sauces and gravies.

The present compounds can also be fortified with vitamins and minerals, particularly the fat-soluble vitamins. The fat-soluble vitamins include vitamin A, vitamin D, vitamin E, and vitamin K. The amount of the fat-soluble vitamins employed herein to fortify the present compounds can vary. If desired, the compounds can be fortified with a recommended daily allowance (RDA), or increment or multiple of an RDA, of any of the fat-soluble vitamins or combinations thereof.

The present compounds are particularly useful in combination with particular classes of food and beverage ingredients. For example, an extra calorie reduction benefit is achieved when the compounds are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The compounds of the present invention can be used in combination with other noncaloric or reduced calorie fats, such as sugar or sugar alcohol fatty acid polyesters, branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the present compounds are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the present compounds in many foods or beverages. The bulking agents can be nondigestible carbohydrates, for example, polydextrose and cellulose or cellulose derivatives, such as carboyxmethylcellulose, carboxyethylcellulose, hydroxypropylcellulose, methyl-cellulose and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

Similarly, foods and beverages can be made that combine the present compounds with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

Many benefits are obtained from the use of the present compounds in foods and beverages, either when used alone or in combination with the ingredients discussed above. A primary benefit is the calorie reduction achieved when the present compounds are used as a total or partial fat replacement. This calorie reduction can be increased by using combinations of the present compounds with reduced calorie sweeteners, bulking agents, or other reduced calorie or noncaloric fats. Another benefit which follows from this use is a decrease in the total amount of triglyceride fats in the diet.

This discussion of the uses, combinations, and benefits of the present compounds is not intended to be limiting or all-inclusive. It is contemplated that other similar uses and benefits can be found that will fall within the spirit and scope of this invention.

The following examples are intended only to further illustrate the invention and are not intended to limit the scope of the invention which is defined by the claims.

EXAMPLE 1

(a) Preparation of an esterified ethoxylated methyl glucoside

An esterified ethoxylated methyl glucoside according to the present invention is prepared as follows. The starting material is "Glucam ® E-20" (Amerchol Corp., Talmadge Rd., Edison, N.J.), which is prepared by reacting 1 mole of methyl glucoside with 20 moles of ethylene oxide to form an ethoxylated methyl glucoside, and which has four primary hydroxyl groups available for reaction with fatty acid chlorides.

Glucam ® E-20 (49.85 g., 0.046 mole) is diluted in DMF (50 ml)/pyridine (100 ml). This solution is charged to a 1 liter, 3-neck round-bottom flask equipped with a reflux condenser, 300 ml cylindrical pressure equalizing addition funnel, thermometer, dry $N_2$ purge and magnetic stirrer. Oleoyl chloride (66.2 g., 0.22 mole) (see part (c) below) is diluted in methylene chloride (225 ml) and the solution placed in the funnel. The reactor's contents are warmed to 40°–45° C. (104°–113° F) and the system purged with dry $N_2$. The oleoyl chloride solution is added dropwise to the stirred contents of the reactor over 1.5 hours. A precipitate of pyridine hydrochloride forms halfway through the addition. After completion of the addition, the reactants are heated to 55° C. (131° F.) for 6 hours. They are then cooled to room temperature and stirred under $N_2$ for an additional 16 hours.

At this point the reaction mixture is transferred to a 2 liter separatory funnel and washed three times with water. The organic phase is then concentrated in a rotary flash evaporator until no additional solvent is removed. The crude product is diluted with methylene chloride and transferred to a separatory funnel. The product is washed three times with 10% HCl. Emulsification of the organic and aqueous phases occurs and requires the addition of small amounts of brine to effect phase separations. The organic phase is then washed with $Ca(OH)_2$ in water. Insoluble calcium oleate salts are removed from the system by suction filtration through a packed Celite (diatomaceous earth) bed and the organic phase washed with neutral brine. The organic phase is then dried over $MgSO_4$ and the desiccant removed by suction filtration. The product is isolated by concentrating it in a rotary flash evaporator at 70° C. (158° F.) until no additional solvent is removed. Yield of the product is 78.5%.

The product is a transparent straw yellow oil with a mild odor reminiscent of leather. It has a low viscosity.

(b) Food compositions according to the present invention

Low calorie fat-containing food compositions are prepared by using the esterified ethoxylated methyl glucoside prepared as described in Example 1 (hereinafter referred to as "ethoxylated glucoside tetraoleate") in the following formulations:

| | Ingredients | % by weight |
|---|---|---|
| Example I - Salad Oils | | |
| (A) | Refined, bleached, and lightly hydrogenated soybean oil | 50 |
| | Ethoxylated glucoside tetraoleate | 50 |
| | | 100 |
| (B) | Refined cottonseed oil | 90 |
| | Ethoxylated glucoside tetraoleate | 10 |
| | | 100 |
| Example II - Plastic Shortening | | |
| (A) | Lightly hydrogenated soybean oil (I.V. 107) | 50 |
| | Ethoxylated glucoside tetraoleate | 40 |
| | Tristearin (hardstock, I.V. 8) | 10 |
| | | 100 |
| (B) | 50/50 mixture of hardened cottonseed oil and lard | 40 |
| | Monoglycerides of soybean oil | 10 |
| | Ethoxylated glucoside tetraoleate | 50 |
| | | 100 |
| Example III - Prepared Cake Mix | | |
| (A) | Specific | |
| | Cake flour | 36 |
| | Sugar | 44 |
| | Shortening (ethoxylated glucoside tetraoleate) | 13 |
| | Nonfat dried milk solids | 4 |
| | Leavening | 2 |
| | Salt | 1 |
| | | 100 |
| (B) | General | |
| | Sugar | 35–50 |
| | Flour | 25–50 |
| | Shortening (ethoxylated glucoside tetraoleate) | 5–30 |
| | Leavening | 1–4 |

-continued

| Ingredients | % by weight |
| --- | --- |
| Cocoa | 0–7 |
| Egg | 0–5 |
| Milk solids | 0–5 |
| Flavor | 0–5 |
| | 100 |

Example IV - Prepared Icing Mix

| | |
| --- | --- |
| Shortening (50/50 mixture of conventional vegetable shortening and ethoxylated glucoside tetraoleate) | 20 |
| Salt | 2 |
| Nonfat dry milk solid | 5 |
| Sugar | 73 |
| | 100 |

Example V - Mayonnaise

| | |
| --- | --- |
| Fat (75:25 blend of ethoxylated glucoside tetraoleate and refined cottonseed oil) | 75 |
| Vinegar | 10 |
| Egg yolk | 9 |
| Sugar | 3 |
| Salt | 1 |
| Mustard | 1 |
| Flavor | 1 |
| | 100 |

Example VI - Salad Dressing

| | |
| --- | --- |
| Fat (ethoxylated glucoside tetraoleate) | 50 |
| Cornstarch | 5 |
| Vinegar | 10 |
| Water | 35 |
| | 100 |

Example VII - Margarine

| | |
| --- | --- |
| Oil (ethoxylated glucoside tetraoleate) | 80 |
| Milk solids | 2 |
| Salt | 2 |
| Monoglyceride | 15 |
| Water | 1 |
| | 100 |

(c) Synthesis of the oleoyl chloride reactant

Following is the preferred method for synthesizing the oleoyl chloride used in making the products of Examples 1 and 2.

Oleic acid (141 g, 0.50 mole) is dissolved in methanol (250 ml) in a 2 liter Erlenmeyer flask and potassium hydroxide pellets (28.2 g, 0.50 mole) added. The mixture is then stirred while the pellets gradually dissolve. After four to five hours, reagent grade acetone (1 liter) is slowly added to the solution and a white precipitate formed. The flask is then stoppered and stored in a freezer overnight. The following day the potassium oleate precipitate is collected by suction filtration and washed on the filer with additional acetone. The potassium oleate is then dried at first in a forced air oven at 50° C. (122° F.) and finally in a vacuum oven at 45° C. (113° F.). Yield of potassium oleate is in the 80 to 90 percent range, about 140 g per batch.

A 5 liter, three-neck round bottom flask is equipped with a refluxing condenser, a magnetic stirrer, a 250 ml cylindrical funnel, and an argon purge. The flask is charged with dry potassium oleate (230 g, 0.72 mole) slurried in 1 to 1 methylene chloride - hexane (2.5 liters) and a few crystals of KCl added to the flask. The flask is then purged with argon gas and kept under a positive head of argon. The entire contents of an ampule of oxalyl chloride (100 g, 0.79 mole) is diluted with methylene chloride (100 ml) and poured into the cylindrical funnel. The oxalyl chloride solution is added dropwise to the slurry with gentle stirring over a 2 to 3 hour period with substantial evolution of $CO_2$ and CO occurring. During the addition the potassium oleate gradually disappears and is replaced by a finer precipitate of KCl. The reaction mixture is allowed to stand under argon with no further agitation overnight. The following day the KCl precipitate is removed from the product solution by suction filtration through a bed of Celite (diatomaceous earth). The filtered solution is then concentrated by rotary flash evaporation until no additional solvent is removed from the product. The product is stored in sealed bottles under argon until used. The oleoyl chloride prepared is a pale yellow oil with a pungent odor. Yield of this reaction is about 90 percent. Confirmation of the product's identity is made by infrared spectroscopy.

EXAMPLE 2

(a) Preparation of an esterified propoxylated methyl glucoside

An esterified propoxylated methyl glucoside according to the present invention is prepared as follows. The starting material is "Glucam ® P-20" (Amerchol Corp., Talmadge Rd., Edison, N.J.), which is prepared by reacting 1 mole of methyl glucoside with 20 moles of propylene oxide to form a propoxylated methyl glucoside. It has four secondary hydroxyl groups available for reaction with fatty acid chlorides.

Glucam ® P-20 (54.1 g., 0.043 mole) is diluted with DMF (50 ml)/pyridine (150 ml) and charged to the reaction apparatus described in Example 1. The reactor's contents are kept at room temperature (21° C., 70° F.) and the system purged with dry $N_2$. Oleoyl chloride (62.4 g., 0.206 mole) is diluted with methylene chloride (160 ml) and added as described in Example 1. After completion of the addition, the reactants are heated to 70°–85° C. (158°–185° F.) and held at that temperature for 18 hours. They are then cooled to room temperature and stirred under argon for an additional 60 hours.

The isolation of the product is similar to that described for the product of Example 1. The organic and aqueous phase emulsions formed by the product are more stable than those of the product of Example 1, but the emulsions are broken by standard techniques of salting and heating. The yield of the product is 87.2%.

The product is a transparent light amber oil with a mild odor reminiscent of leather. It has a low viscosity.

(b) Food compositions

Low calorie food compositions are prepared using the recipes of Example 1, by replacing the ethoxylated glucoside tetraoleate of Example with the product described hereinabove in Example 2.

EXAMPLE 3

(a) Preparation of an esterified ethoxylated methyl glucoside

An esterified ethoxylated methyl glucoside according to the present invention is prepared as follows. The product is similar to that of Example 1, except that it is esterified with stearoyl chloride instead of oleoyl chloride.

Glucam ® E-20 (49.9 g., 0.040 mole) (Amerchol Corp., Edison, N.J.) is diluted with DMF (50 ml)/pyridine (100 ml) and charged to the reaction apparatus described in Example 1. The reactor's contents are warmed to 40°–45° C. (104°–113° F.) and the system purged with dry N₂. Stearoyl chloride (66.2 g., 0.22 mole) (Eastman Kodak, Rochester, NY, Catalog No. 113 9450) is dissolved in methylene chloride (22.5 ml) and added dropwise to the reactor over 1 hour. The reaction is conducted as described in Example 2. Isolation of the product is done using the same procedures described in Example 1. The overall yield of product is 84.8%.

The product is a light tan solid at room temperature with a sharp melting point at 36–37° C. (97°–99° F.). Above this temperature, the product is a light amber oil of low viscosity. It has a pungent, mildly unpleasant odor.

(b) Food compositions

Low calorie food compositions are prepared using the ethoxylated glucoside tetrastearate prepared as described in Example 3 in the following formulations:

| Ingredients | % by Weight |
|---|---|
| Example I - Plastic Shortening | |
| Ethoxylated glucoside tetrastearate | 50 |
| 50/50 mixture of hardened cottonseed oil and lard | 40 |
| Monoglycerides of soybean oil | 10 |
| | 100 |
| Example II - Prepared Cake Mix | |
| Cake flour | 36 |
| Sugar | 44 |
| Ethoxylated glucoside tetrastearate | 13 |
| Nonfat dried milk solids | 4 |
| Leavening | 2 |
| Salt | 1 |
| | 100 |

What is claimed is:

1. A low calorie fat-containing food composition which comprises non-fat ingredients and fat ingredients, from about 10% to about 100% by weight of said fat ingredients consisting essentially of a fatty acid ester of an alkoxylated alkyl glycoside, wherein:
   (a) the glycoside molecule has one alkyl group attached through a hemiacetal bond, and wherein the alkyl group contains between 1 and 22 carbon atoms;
   (b) between 1 and about 50 alkoxyl groups are attached by ether linkages to each alkyl glycoside molecule, and not more than about 12 alkoxyl groups are attached to each attachment site of an alkyl glycoside molecule;
   (c) each alkoxylated alkyl glycoside molecule is esterified with between 4 and 7 fatty acid groups, and wherein the fatty acids contain between about 2 and about 24 carbon atoms; and
   (d) the alkoxyl group is derived from the cyclic ether ethylene oxide.

2. A food composition according to claim 1 wherein the alkyl group is selected from the group consisting of methyl, ethyl and butyl, and mixtures thereof.

3. A food composition according to claim 1 wherein the alkyl glycoside is a methyl glucoside.

4. A food composition according to claim 1 wherein between about 6 and about 30 alkoxyl groups are attached to each alkyl glycoside molecule.

5. A food composition according to claim 1 wherein between about 1 and about 8 alkoxyl groups are attached to each attachment site of an alkyl glycoside molecule.

6. A food composition according to claim 1 wherein the fatty acids contain between about 8 and about 22 carbon atoms.

7. A food composition according to claim 1 wherein from about 10% to about 100% by weight of said fat ingredients consist essentially of an esterified ethoxylated methyl glucoside having the structural formula:

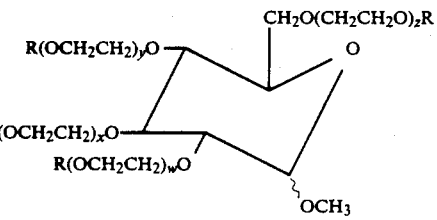

wherein:
   $w+x+y+z$ is from 1 to about 50; each w, x, y, and z has a numerical value of not more than about 12; and each R is a fatty acyl group having between about 2 and about 24 carbon atoms.

8. A food composition according to claim 7 wherein $w+x+y+z$ is from about 6 to about 30.

9. A food composition according to claim 7 wherein each w, x, y, and z has a numerical value between about 1 and about 8.

10. A food composition according to claim 7 wherein R is a fatty acyl group having between about 8 and about 22 carbon atoms.

11. A food composition according to claim 5 wherein between about 2 and about 6 alkoxyl groups are attached to each attachment site of an alkyl glycoside molecule.

12. A food composition according to claim 9 wherein each w, x, y and z has a numerical value between about 2 and about 6.

* * * * *